United States Patent [19]

Yquel

[11] 4,392,384

[45] Jul. 12, 1983

[54] MEASURING INSTRUMENT WITH AUTOMATIC LOADING AND AN AUTOMATIC CYCLE, FOR STUDYING THE TENSILE CHARACTERISTICS OF FIBRES

[75] Inventor: Jean-Pierre Yquel, Colombes, France

[73] Assignee: L'Oreal, Paris, France

[21] Appl. No.: 301,833

[22] Filed: Sep. 14, 1981

[30] Foreign Application Priority Data

Sep. 22, 1980 [FR] France ................. 80 20331

[51] Int. Cl.³ .............................................. G01N 3/08
[52] U.S. Cl. .................................................... 73/830
[58] Field of Search ................. 73/828, 826, 830, 840, 73/831, 834

[56] References Cited

U.S. PATENT DOCUMENTS

| | | |
|---|---|---|
| 3,067,607 | 12/1962 | Crane et al. |
| 3,474,524 | 10/1969 | Huggins ................. 29/505 |
| 3,504,536 | 4/1970 | Baker et al. ................. 73/828 |
| 3,921,443 | 11/1975 | Yates . |

FOREIGN PATENT DOCUMENTS

| | | |
|---|---|---|
| 808256 | 2/1937 | France . |
| 1438448 | 4/1966 | France . |
| 1479280 | 3/1967 | France . |
| 2149104 | 3/1973 | France . |
| 2232247 | 12/1974 | France . |
| 2386044 | 10/1978 | France . |

OTHER PUBLICATIONS

Antsiferov, V. N. Equipment for testing ... Fibers from Industrial Laboratory, vol. 43, No. 6, Jun. 1977, pp. 844 and 845.

Primary Examiner—Jerry W. Myracle
Attorney, Agent, or Firm—N. Jerome Rudy

[57] ABSTRACT

A measuring instrument for studying the tensile characteristics of hair or other fibre samples is provided with elements whereby it is possible successively to carry out measurements on a series of samples automatically without intervention by an operator. A stack of pairs of blocks (12A and 12B) is mounted in a loader (23) with a sample (21) connected between the blocks of each pair. The sample blocks are displaceable as a pair from the bottom of the loader across a plate to be engaged by relatively movable clamps (11 and 19) by means of which the sample carried between the blocks can be stretched. A dynamometer (5) measures the tension for a predetermined elongation and a sensor (54) cooperating with an anvil (25) senses changes in transverse dimensions of the sample.

19 Claims, 9 Drawing Figures

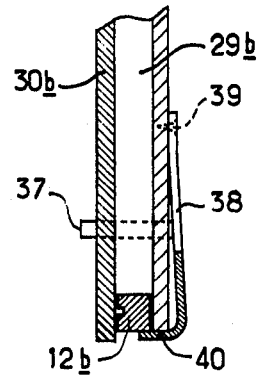
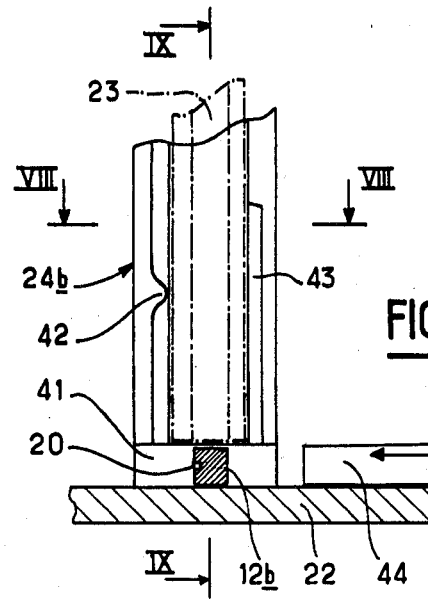
FIG. 6
FIG. 7
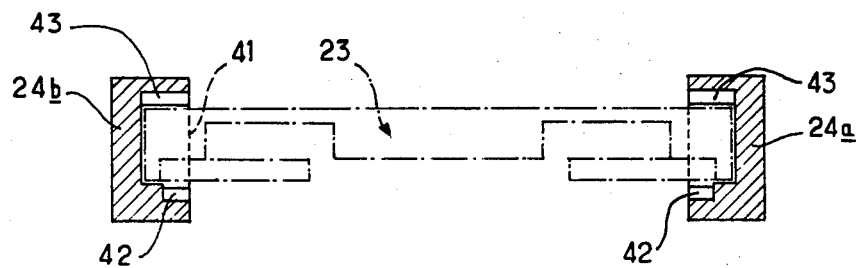
FIG. 8
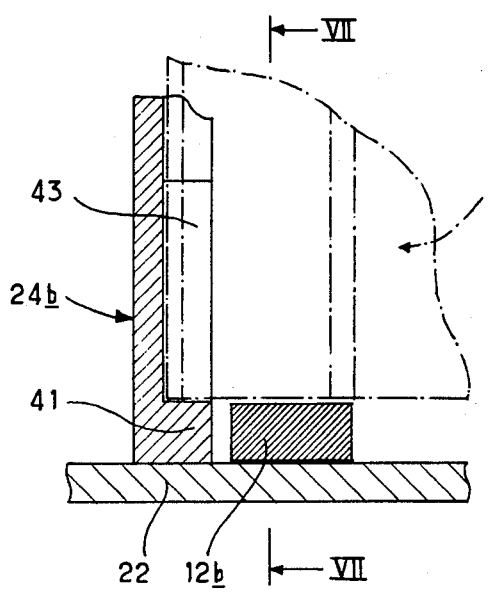
FIG. 9

MEASURING INSTRUMENT WITH AUTOMATIC LOADING AND AN AUTOMATIC CYCLE, FOR STUDYING THE TENSILE CHARACTERISTICS OF FIBRES

DESCRIPTION

The present invention relates to an instrument which makes it possible to measure the elongations under tension and the corresponding tensile forces for fibres or analogous materials. More especially the instrument makes it possible successively to carry out measurements on a group of samples automatically, it being possible for the results to be recorded without any intervention by the operator.

It is known that it is frequently desirable to study the characteristics of a category of fibres when these fibres are subjected to a certain number of treatments; this is the case, in particular, of keratin fibres and especially of human hair. If it is desired to study the effect of a cosmetic or pharmaceutical treatment on hair, it is necessary to study, inter alia, their tensile characteristics; to do this, it is necessary to apply an increasing tensile force to a hair and to measure its elongation as a function of the stress applied. In general, the tensile force is measured for a given percentage elongation, for example 15%, and the percentage elongation at break and the breaking load are also measured. However, it is very clear that a study of this type can only provide usable information insofar as it is conducted statistically, that is to say that it is necessary to repeat the measurements on a large number of hairs which have been subjected to the same treatment. Consequently, it is desirable to have available a measuring instrument which makes it possible to carry out the desired measurements repeatedly and automatically; otherwise, the working time required to obtain the results is too long; furthermore, if the operator must intervene for each measurement, the measuring time increases and the operator is obliged to perform a tedious task.

The object of the invention is thus to provide a measuring instrument which is capable of studying the tensile characteristics of fibres, and in particular of hair, this instrument being arranged so as to carry out the desired tests automatically on a group of samples taken successively by the instrument, without the operator having to intervene. Furthermore, it has been found that it is frequently necessary, in order to utilise the measurements made in this way, to have a measurement of the transverse dimension of the fibre studied; the measurements can thus be related to a fibre having a reference cross-section of unity, and this makes it possible to improve the utilisation of the measurement results. The present instrument also makes it possible to evaluate the transverse dimension of the fibre under test, before carrying out the tensile test; thus, all the parameters permitting the study to be carried out, that is to say the transverse dimension of the fibre, the elongation and the tensile stress, are obtained simultaneously. The value of the instrument is that it does not require any manual intervention during the course of a series of measurements carried out on a series of samples prepared beforehand; the results can either be read off on meters for each test, or recorded directly, in which case even the presence of the operator is no longer essential.

On account of the rapid operating speed of the automatic instrument, a single instrument can be supplied by series of samples prepared by several operators, the samples being placed in loaders which are positioned on the instrument when a measurement sequence has ended, that is to say when all the samples in one loader have been tested.

The instrument as later described in detail is capable of providing a measurement of the tensile force for a predetermined percentage elongation of the fibre tested; this percentage can be adjusted, without difficulty, to the desired value, according to the fibre to be studied. However, it is also possible to record the variation in the elongation as a function of the tensile force, it being possible for the result to provide a trace, on a recorder, of a curve extending as far as the breaking point of the fibre.

The present invention consequently relates to the new industrial product consisting of a measuring instrument for measuring the deformations of and tensile forces in a sample fibre or analogous material when subjecting the sample to a longitudinal tensile stress, said instrument comprising a frame; a tensioning means carried on the frame and including a movable element to be associated with one, movable, end of a sample to be tested; a force detector also carried on the frame and including means to be associated with the other, fixed, end of the sample; a feed plate; a plurality of pairs of sample blocks with the sample blocks of each pair being provided with means firmly to hold opposite ends of a sample to be tested; a sample loader provided with means to receive a plurality of said pairs of sample blocks stacked with the samples carried thereby parallel one with the other, said sample loader having a discharge axis perpendicular to the direction of extent of said samples and being held fixed relative to the frame with the extent of the stack perpendicular to said feed plate; a feed device capable of pushing a pair of sample blocks perpendicularly to a plane formed by the samples in the loader while said pair of sample blocks is carried by the feed plate from an initial position located in line with the loader, with simultaneous translational movement of the two sample blocks to a loaded position; two clamps one of which is fixed and cooperates with the force detector while the other cooperates with the movable element of the tensioning means, said sample blocks in their loaded position being received in said clamps, the said feed device being retractable to its initial position to engage a new pair of sample blocks carried by the feed plate; control means for triggering the operation of the tensioning means when the sample blocks are in position in the said clamps; one measuring means, associated with the force detector, providing the value of the tensile force applied to the sample; other measuring means, associated with the movable element of the tensioning means, providing the value of the elongation of the sample; and means for returning the tensioning means to an initial position after its movable element has been subjected to sufficient translational movement for the measurement, said feed device being operable, when bringing a new pair of sample blocks into the clamps, to cause the previous two sample blocks to be driven out from the said clamps.

In a preferred embodiment, the instrument also comprises a means for measuring a transverse dimension of the fibre fixed between the two sample blocks, the said means being arranged between the two clamps and consisting of a sensor supported by a movable arm and arranged in line with an anvil carried by the frame, the said anvil being between the two clamps and below the fibre of the sample, the blocks of which are held by the said clamps; the sensor possesses a plate which rests on the fibre to be measured, which fibre is supported by the anvil, the said plate being integral with a rod which carries a magnet cooperating with a displacement detector carried by the frame, and the said rod being carried by the movable arm when it is not resting on the fibre; and the displacement of the movable arm is controlled by a reversible electric motor.

Preferably, the blocks arranged at the ends of fibre to be tested are rectangular parallelepipeds possessing a groove into which the said fibre ends are inserted; the loader comprises two identical parallel slides having the dimensions of the sample blocks, the distance between the adjacent edges of the two slides being substantially equal to the length of the fibre to be tested; in its bottom part, the loader comprises at least one stud which controls at least one retaining plate preventing the blocks contained in the loader from falling, the loader being held relative to the frame by engagement between two guides perpendicular to the feed plate, and the stud(s) cooperating with the said guides to release the said retaining plate (or plates) when the loader is positioned in its guides, and this enables the first sample to be tested to fall onto the feed plate; the loader is associated with an inertia block which rests with its weight on the stack of sample blocks contained in the loader, and which descends towards the feed plate as the loader empties, the said inertia block cooperating with at least one fixed contact to indicate when the loader is full.

Advantageously, the feed device comprises a fork which undergoes translational movement on the feed plate by virtue of a pneumatic, hydraulic, electric or electromagnetic jack, each arm of the fork cooperating with one of the sample blocks to be displaced; at least one of the two clamps comprises a stop cooperating with the other clamp to define the minimum distance between the clamps; the stop consists of a fork, the anvil being arranged between the two arms of the said fork. In the preferred embodiment, the tensioning means consists of a reversible electric motor which is associated with a screw-and-nut system; the motor drives a screw and the movable clamp is integral with a nut carrying at least one stud which slides in a groove fixed relative to the frame; the displacement of the movable clamp is measured by a detector producing an electric signal, the measurement being started when the tensile force becomes non-zero; the force detector is a dynamometric ring which is joined at one point to the frame, the said ring carrying at least one stress gauge producing an electric measuring signal; the fixed clamp is integral with a rod which passes through the dynamometric ring and rests on a point inside the latter by means of a rounded bearing, the said rod being guided, with play, relative to the frame; the dynamometric ring carries four stress gauges which are connected to form a bridge and are distributed in pairs at the ends of a diameter of the ring which is substantially perpendicular to the rod exerting the tension; on that side of the anvil which is opposite the feed plate, there is an inclined plane ensuring the discharge of the blocks which are ejected from the clamps when the latter are re-loaded.

To provide a clearer understanding of the subject of the invention, an embodiment thereof, shown in the accompanying drawing, will now be described by way of a purely illustrative and non-limiting example.

Figure 3:
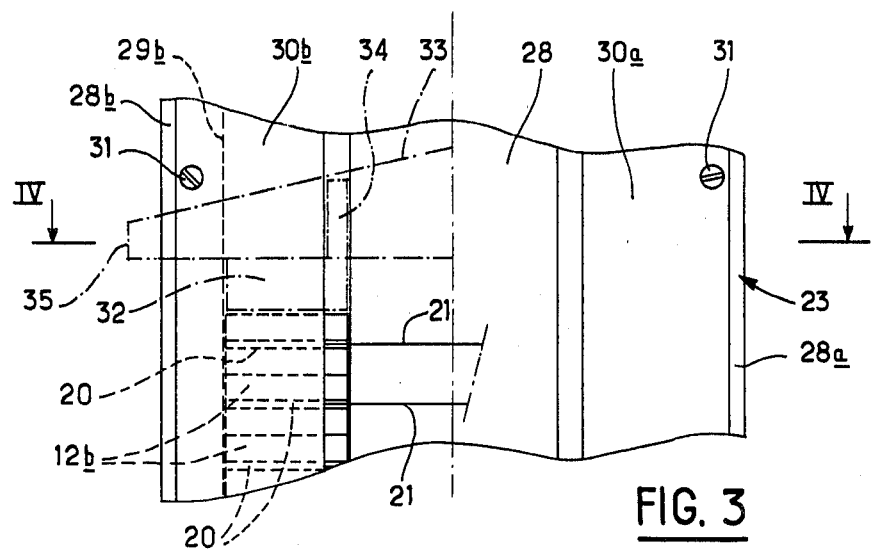
Figure 4:
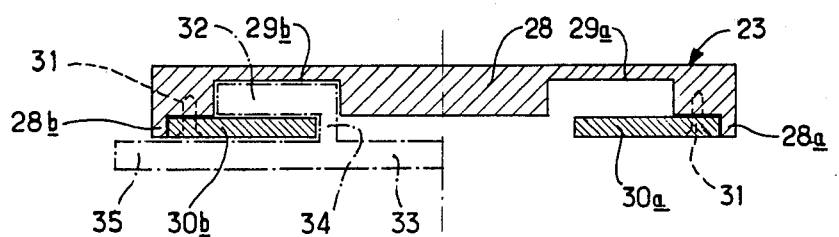
Figure 5:
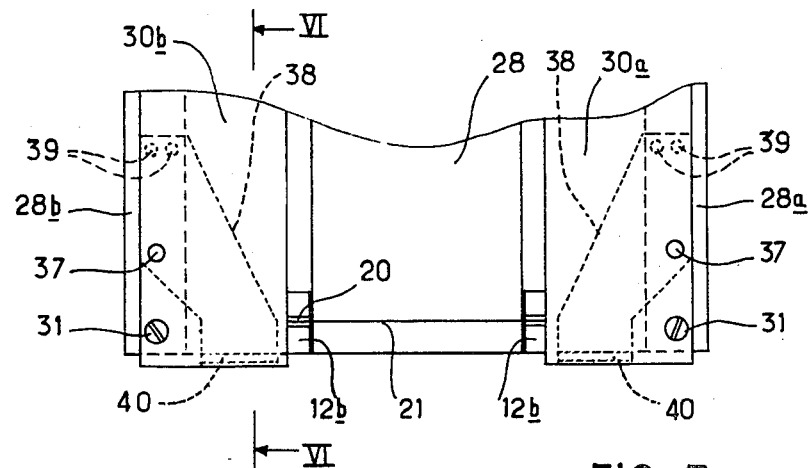

FIG. 3 shows a portion of the sample loader of the instrument, this loader being shown in a side view, the left-hand part of FIG. 3 showing three sample blocks positioned in the slide of the loader, these three blocks being represented in broken lines and being surmounted by an inertia block shown in dot-and-dash lines in the drawing, and the right-hand part of FIG. 3 showing the external appearance of the empty loader;

FIG. 4 shows a section taken along line IV—IV of FIG. 3;

FIG. 5 shows the base of the sample loader of the instrument;

FIG. 6 shows a section taken along line VI—VI of FIG. 5;

FIG. 7 shows the base of one of the two fixing guides of the loader of the instrument, this representation corresponding to a section taken along line VII—VII of FIG. 9, the loader being shown in dot-and-dash lines;

FIG. 8 shows a section taken along line VIII—VIII of FIG. 7, the loader being shown in dot-and-dash lines; and FIG. 9 shows a section taken along line IX—IX of FIG. 7, the loader being shown in dot-and-dash lines.

With reference to the drawing, it is seen that the frame of the instrument comprises a baseplate 1 to which are fixed the support 2 of a tensioning means consisting of a reversible electric motor 3 and the support 4 of a dynamometric ring 5. The dynamometric ring 5 is fixed to the support 4 by screws 6 and it carries, at its top and bottom points, a pair of stress gauges 7, the four gauges 7 being connected to form a bridge in order to produce an electric signal which gives a measurement of the force applied to the ring 5 by a rod 8 arranged along the horizontal diameter of the ring 5. The rod 8 passes through the ring 5 via an orifice 9 and rests on the inside face of the ring 5 by means of a rounded bearing 10 provided on a zone 8a of the rod 8, which has a larger diameter than that of the rod 8 outside the ring 5. The part 8a of the rod 8 slides in an arm 4a of the support 4 with sufficient play to give a relative orientation of the ring 5 and the rounded bearing 10 to enable the applied force to be measured with the optimum precision. The rod 8 is joined to a fixed clamp 11 which makes it possible to receive the block 12a constituting one of the ends of the sample under test.

The support 2 is joined by a cylindrical casing 13 to an intermediate support 14 carried by the baseplate 1. The cylindrical casing 13 is joined to the supports 2 and 14 by means of flanges 13a, 13b respectively. A screw 15, driven by the rotor of the motor 3, is arranged inside the cylindrical casing 13. The screw 15 engages with the internal thread of an internally threaded tube 16, the said tube being capable of sliding freely inside the cylindrical casing 13. On its external surface, the tube 16 comprises a stud 17 which can undergo a translational movement in a groove 18 made along a generatrix of the cylindrical casing 13, starting from the flange 13b, and over a sufficient length to enable the movable element formed by the tube 16 to have the desired travel. A movable clamp 19, where a block 12b can be housed which is firmly fixed to that end of the sample which is opposite the one carrying the block 12a, is fixed to the end of the tube 16. The axes of the tube 16 and of the rod 8 are aligned.

The blocks 12a and 12b are identical. They each consist of a stainless steel rectangular parallelepiped which has a substantially square cross-section and which possesses a groove 20 on one of its large faces. The sample which is tested by means of the instrument according to the invention consists of a fibre 21, for example a hair, the ends of which are arranged in the grooves 20 in two blocks 12a, 12b; the fibre 21 is fixed in the grooves 20 by means of glue. The block 12a is held in the clamp 11, on the one hand by a top plate 11a and on the other hand by a front plate 11b. The block 12b is held in the clamp 19, on the one hand by a top plate 19a and on the other hand by a front plate 19b, the said plate 19b being extended in the direction of the front plate 11b by a substantially horizontal fork 19c. The ends of the arms of the fork 19c can butt against the front plate 11b when the movable clamp 19 moves as close as possible towards the fixed clamp 11. The travel of the movable clamp 19 is thus limited by the resting of 19c against 11b and by the resting of the stud 17 on the bottom of the groove 18. The arrival at the ends of the travel can be detected by the blocking of the rotor of the motor 3 or by micro-contacts not shown in the drawing.

The lower face of the two blocks 12a, 12b is exactly at the level of the upper face of a horizontal feed plate 22. As will be described in detail below, the feed plate 22 makes it possible to supply the clamps 11–19 with samples from a loader 23. The loader 23 has the shape of a flat rectangular parallelepiped, the mean plane of which is arranged perpendicularly to the feed plate 22 and parallel to the fibre 21 of the sample to be tested. The loader 23 is held in position by means of two guides 24a, 24b, which are symmetrical relative to a plane and perpendicular to the feed plate 22. The guides 24a, 24b each have a U-shaped horizontal cross-section, the arms of the U being opposite one another. An anvil 25 is arranged between the front plates 11b and 19b and below the fibre 21; the anvil 25 is a cylinder with a vertical generatrix and a circular horizontal cross-section; it is supported by the baseplate 1 via a frustoconical base 26; the two arms of the fork 19c pass either side of the base 26. An inclined plane 27, which slopes from the clamps 11 and 19 down to the baseplate 1, has been positioned on that side of the clamps 11 and 19 where the feed plate 22 is not located.

Figure 1:
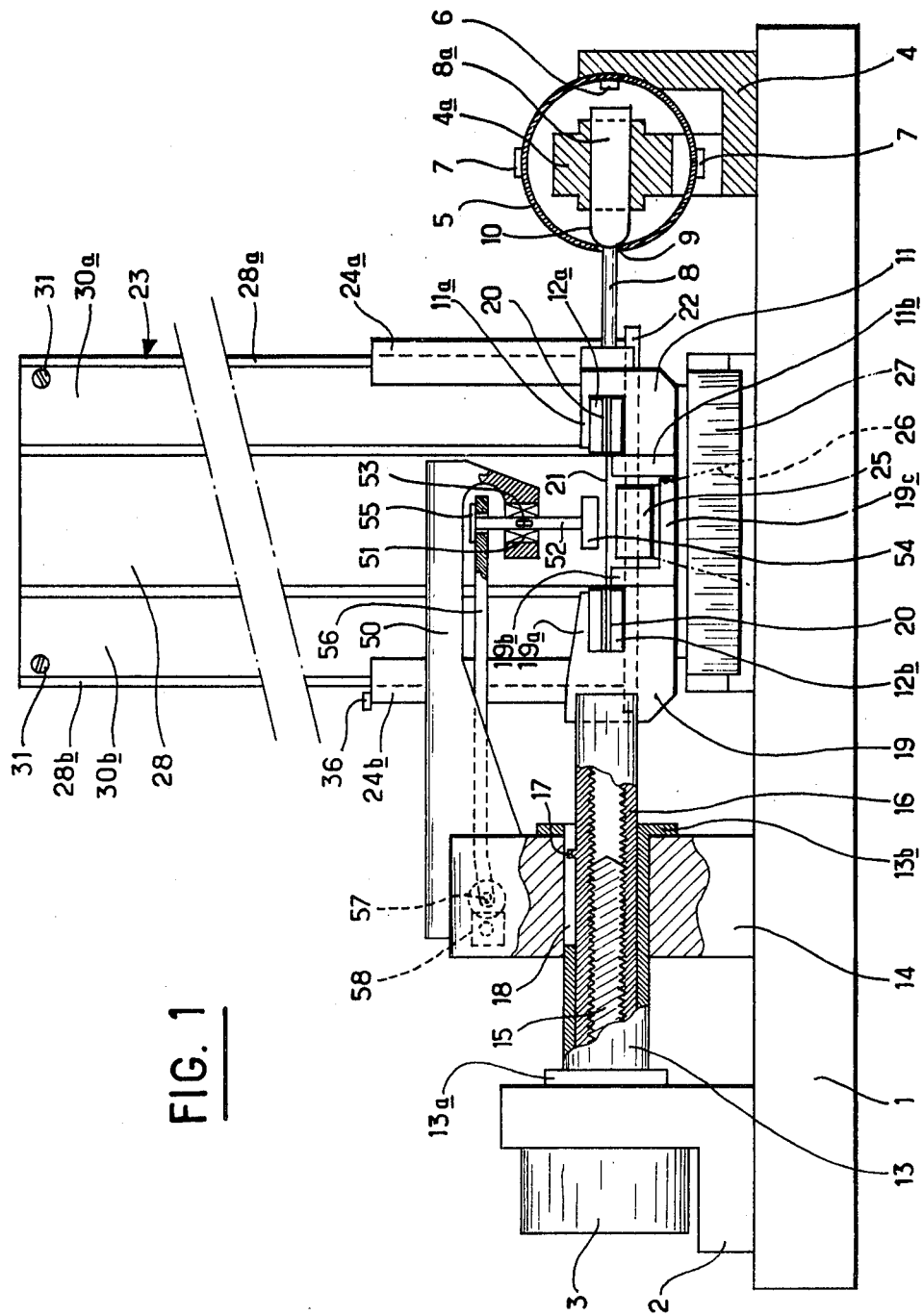
FIG. 1 shows a side view of an instrument embodying the invention, certain parts of which have been shown in section.
Figure 2:
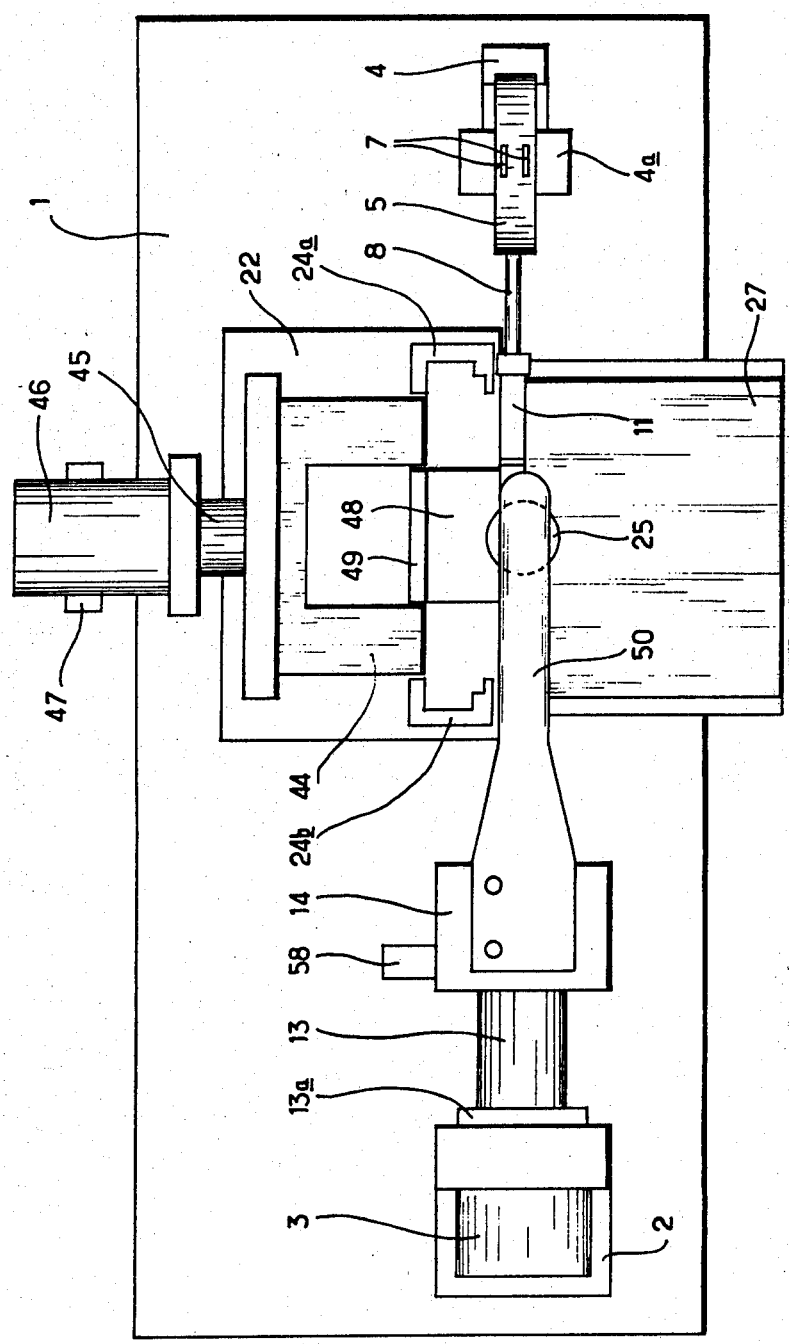
FIG. 2 shows the instrument of FIG. 1 viewed in plan, the sample loader being omitted.

The loader 23 consists of a backplate 28 having a rectangular shape in plan; along the two large sides of the backplate 28, there are two projecting ribs 28a, 28b; two grooves 29a, 29b, which form slides for the blocks 12a, 12b respectively, have been made in the bulk of the backplate, symmetrically relative to the mean longitudinal line of the said backplate. The blocks 12a, 12b are located in the grooves 29a, 29b so that the grooves 20 are located on the side opposite the backplate 28; the length of the blocks 12a, 12b, that is to say the length of the grooves 20, is exactly equal to the width of the slides 29a, 29b; the thickness of the blocks 12a, 12b, measured perpendicularly to the plane of FIG. 1, is slightly greater than the depth of the slides 29a, 29b. In the loader 23, the blocks 12a, 12b of two successive samples are superposed and bear on one another. When it is filled with samples, the loader 23 thus possesses a stack of blocks 12a in its slide 29a and a stack of blocks 12b in its slide 29b. On the side where the backplate 28 is not located, the slides 29a, 29b are closed by detachable plates 30a, 30b respectively, the said detachable plates being secured by means of screws 31. The plates 30a, 30b are flush at the same level as the edges 28a, 28b and their width is such that a small part of the blocks 12a, 12b stacked in the loader can be seen. The two feet 32 of an inertia block 33 are positioned in the grooves 29a, 29b, above the stack of blocks 12a, 12b. The inertia block 33 is arranged outside the loader 23, in front of the latter, that is to say on the same side as the clamps 11 and 19; it is joined to the feet 32 by limbs 34 which pass through the gaps existing between the backplate 28 and the detachable plates 30a and 30b. The inertia block 33 is a little wider than the loader 23 and, with one of its lateral ends 35, it controls a micro-contact 36 placed in the upper part of the guide 24b. In this way, when the loader is nearly empty, a sound signal is operated, which indicates to the operator that it will soon be necessary to replace the loader of the instrument.

As shown clearly in FIGS. 5 and 6, the loader 23 comprises, in its bottom part, two studs 37 arranged at exactly the same distance from the lower edge of the loader, along the edges 28a, 28b. The studs 37 each act on a leaf spring 38 arranged behind the backplate 28 and fixed to the latter by means of screws 39. The leaf springs 38 are bent to form a right angle so that they form a retaining plate 40 at the bottom part of each of the slides 29a, 29b. The retaining plates 40 prevent the stacks of blocks 12a and 12b from falling under gravity while the studs 37 are in the projecting position. When the loader 23 is positioned in its guides 24a, 24b, the lower edge of the loader 23 rests on the bases 41 of the two guides 24a, 24b, and, in this position, the distance existing between the feed plate 22 and the lower edge of the loader 23 is equal to the height of the blocks 12a, 12b. In this position, the stud 37 is pushed in by a boss 42 provided in the guides 24a, 24b, so that, as soon as the loader 23 has been positioned, the retaining plates 40 are released; as a result, the two blocks 12a, 12b of the first sample to be tested fall onto the feed plate 22 in line with the loader 23. So that the retaining plates 40 can be released, the leaf springs 38 must be disengaged towards the rear of the loader, and, to do this, a recess 43 has been provided in the rear wing of the guides 24a, 24b.

Behind the guides 24a, 24b and the loader 23, that is to say on the side where the clamps 11 and 19 are not located, a feed device comprising a fork 44 is provided, which fork slides over the feed plate 22 and is pushed by the piston 45 of a jack 46 carried via the baseplate 1 by the support 47. The two arms of the fork 44 pass between the guides 24a, 24b, below the loader 23; they are arranged on either side of a centering rib 48 of which a projection 49, pointing upwards, cooperates with the middle of the rear face of the backplate 28 of the loader 23. When it is pushed by the piston 45 of the jack 46, the fork 44 engages under the loader 23 and pushes the blocks 12a and 12b of the sample, which is in line with the loader 23, until they are in the housing provided for the purpose in the clamps 11 and 19 respectively. If these clamps already contain blocks 12a, 12b at the time of loading, the blocks 12a, 12b being located out the previous blocks, which then fall on the inclined plane 27 and slide under gravity down to the baseplate 1 of the instrument. When loading has been carried out, the fork 44 is controlled so as to perform a reverse movement; while it is in line with the loader 23, it supports the stack of blocks 12a, 12b contained in this loader. As soon as its backward movement is sufficient, the stacks of blocks 12a, 12b are no longer supported and a new pair of blocks 12a, 12b falls onto the feed plate 22 in line with the loader 23; this new sample is the one which is intended for the next loading.

The instrument illustrated also makes it possible to measure a transverse dimension of the fibre 21 under test. To do this, the intermediate support 14 carries a crosspiece 50 which, at its end, supports a displacement detector 51. The displacement detector 51 consists of a set of windings which cooperate with a rod 52 passing through the said windings; the rod 52 carries a permanent magnet 53 arranged at the level of the detector 51, so that any displacement of the rod 52 relative to the detector 51 results in the provision of an electric signal by the detector, the said signal making it possible to measure the displacement. The rod 52 terminates towards the bottom in a plate 54 and towards the top in a disc 55; the plate 54 and the disc 55 are perpendicular to the axis of the rod 52. The plate 54 is intended to act as a sensor and to rest on the fibre 21; the disc 55 is intended to ensure the raising of the rod 52 by a movable arm 56 which is substantially parallel to the crosspiece 50. The rod 52 passes through the arm 56, and the disc 55 can simply rest on the upper face of the arm 56.

The arm 56 is capable of pivoting about the axis of a shaft 57 which is caused to rotate by means of a step-down motor 58. The position adopted by the magnet 53 when the plate 54 comes to rest directly on the anvil 25 is known. When the arm 56 is lowered by means of the step-down motor 58, the plate 54 comes to rest on the fibre 21 and this results in a modification of the position of the magnet 53 relative to the windings of the displacement detector 51; from this difference in position, the thickness of the fibre 21, that is to say a transverse dimension of the said fibre, is deduced. It is very clear that, if the fibre were perfectly cylindrical, it is the diameter of the fibre which would be measured in this way, but, in reality, numerous natural fibres are not perfectly cylindrical and it is for this reason that, in the present description, it is indicated that a transverse dimension of the fibre under test, and not the diameter of the said fibre, is measured. When this transverse dimension has been measured, it suffices to raise the arm 56 by means of the step-down motor 58 for the plate 54 to be released and for the tensile test to be carried out without any perturbation.

The sequence of operations in a measurement is as follows: in a first stage, a loader is prepared as will be indicated below. The loader 23 is positioned in its guides 24a, 24b until its lower edge is resting on the bases 41 of the said guides. At this moment, a sample consisting of the assembly comprising two blocks 12a, 12b, joined to one another by a fibre 21, falls onto the feed plate 22. In this position, the instrument is ready to start a sequence of measurements.

The operator controls the start of the sequence by hand. The supply to the step-down motor 58 is switched on in order to lower the arm 56 until the plate 54 comes to rest on the fibre 21 supported by the anvil 25; the result of the measurement provided by the detector 51 is then recorded and/or displayed. Automatically, the step-down motor 58 is then driven in the opposite direction to the above and it thus ensures the raising of the movable arm 56 and, via the disc 55, of the plate 54. An end-of-travel switch makes it possible to stop this movement and to control the supply to the motor 3, which causes the rotation of the screw 15. This ensures displacement of the clamp 19 towards the left in FIG. 1; at the start of the movement, the fork 19c is butting against the front plate 11b. When the clamp 19 moves away from the clamp 11, the fibre 21 is placed under tension. As soon as a force is exerted on this fibre, the rod 8 transmits it to the dynamometric ring 5, via the rounded bearing 10, so that the stress gauges 7 produce an electric signal which gives the measurement of the tensile force. As soon as a tensile force appears, a displacement detector (not shown) detects the displacement of the clamp 19 and it is thus possible to measure the percentage elongation of the fibre 21 under the effect of the tensile stress. The elongation and force measurements can be carried continuously and recorded in order to produce a curve, or alternatively the tensile force can be measured solely when a predetermined percentage elongation, for example 15%, is reached. In all cases, the measurements can be recorded and/or displayed. The tensioning of the sample is continued until the fibre 21 breaks. At this moment, the force measured by the dynamometric ring 5 becomes zero and this causes the supply to the motor 3 to be reversed in order to bring the clamp 19 back to its starting position. When the latter has been reached, the rotor of the motor 3 is blocked because the fork 19c butts against the front plate 11b and the supply to the motor 3 is then automatically cut off. The jack 46 is then controlled automatically so as to cause the fork 44 to advance, and this fork brings a new sample into the clamps 11 and 19, the positioning of this new sample causing the two blocks 12a, 12b of the previous sample to be ejected. When the fork 44 has arrived at the end of its travel, the reverse movement of the jack 46 is automatically controlled and the fork 44 returns to its initial position, which brings a new sample onto the feed plate 22, in line with the loader 23. As soon as the backward movement of the fork 44 is controlled, the step-down motor 58 is controlled automatically and a new measurement cycle is thus started. When the last sample in the loader 23 is introduced into the clamps 11, 19, the feet 32 of the inertia block 33 come to rest on the plate 22 and, in this position, the inertia block 33 controls, by a micro-contact, the stopping of the sequence after the end of the test which has been started.

It is seen that the instrument above described thus makes it possible to carry out the measurements of transverse dimension, elongation and tension on a whole series of samples taken in succession, the sequence being entirely automatic. The results can be recorded graphically and/or can produce printing on a printer, or can also simply be displayed if an operator is watching the sequence of measurements.

To prepare a sample loader, a preparation loader is used, which is identical to the loader 23 except that the detachable plates 30a, 30b are not in position. The preparation loader is placed horizontally on a support and the operator arranges the blocks 12a and 12b, side by side, in the appropriate slides. Between the blocks 12a, 12b of a sample, the operator arranges a fibre 21 to be tested, in the groove 20 in each of these blocks, and he sticks the said fibre inside the grooves 20. When the glue has dried, the fibre 21 joins the two blocks 12a, 12b and passes in front of the central part of the backplate 28 of the loader. When a preparation loader of this type has been set up, it suffices to bring it to the end of a loader 23 fitted with its detachable plates 30a, 30b, and to push the stack of samples into the loader 23. The loader 23 can then be placed in a vertical position, since the stacks of blocks are held by means of the retaining plates 40.

It is seen that the preparation of the samples can be carried out on a large scale and that several operators can simultaneously prepare loaders of samples to be tested by the same instrument. Because of the automation of the operation of the instrument, it is possible to carry out the measurements on a large number of samples, so that the results can have a very satisfactory statistical interpretation, the said interpretation taking into account the measurements of the transverse dimension of the fibre, if appropriate.

I claim:

1. In a measuring instrument for measuring the deformations of and tensile forces in a sample fibre or analogous material when subjecting the sample to a longitudinal tensile stress and which comprises a frame, a tensioning means carried on the frame and including a movable element to be associated with one, movable, end of the sample and a force detector also carried on the frame and including means to be associated with the other, fixed, end of the sample, the improvement in that the said instrument comprises a feed plate; a plurality of pairs of sample blocks with the sample blocks of each pair being provided with means firmly to hold opposite ends of a sample to be tested; a sample loader provided with means to receive a plurality of said pairs of sample blocks stacked with the samples carried thereby parallel one with the other, said sample loader having a discharge axis perpendicular to the direction of extent of said samples and being held fixed relative to the frame with the extent of the stack perpendicular to said feed plate; a feed device capable of pushing a pair of sample blocks perpendicularly to a plane formed by the samples in the loader while said pair of sample blocks is carried by the feed plate from an initial position located in line with the loader, with simultaneous translational movement of the two sample blocks to a loaded position; two clamps one of which is fixed and cooperates with the force detector while the other cooperates with the movable element of the tensioning means, said sample blocks in their loaded position being received in said clamps, the said feed device being retractable to its initial position to engage a new pair of sample blocks carried by the feed plate; control means for triggering the operation of the tensioning means when the sample blocks are in position in the said clamps; one measuring means, associated with the force detector, providing the value of the tensile force applied to the sample; other measuring means, associated with the movable element of the tensioning means, providing the value of the elongation of the sample; and means for returning the tensioning means to an initial position after its movable element has been subjected to sufficient translational movement for the measurement, said feed device being operable, when bringing a new pair of sample blocks into the clamps, to cause the previous two sample blocks to be driven out from the said clamps.

2. An instrument according to claim 1, which comprises means arranged between the clamps for measuring a transverse dimension of a sample fixed between two sample blocks held in said clamps.

3. An instrument according to claim 2, wherein the means for measuring a transverse dimension of the sample comprises an anvil carried by the frame and located between the clamps and below the positions of a sample under test, a sensor, and a movable arm supporting said sensor in line with said anvil.

4. An instrument according to claim 3, wherein the sensor comprises a sensor plate for resting on the sample under test while said sample is supported by the anvil, a rod integral with said sensor plate, a magnet carried by said rod, and a displacement detector carried by the frame and cooperable with said magnet, the said sensor rod being supported by the movable arm when the sensor plate is not resting on and supported by said sample.

5. An instrument according to claim 3, wherein a reversible electric step-down motor is provided to control the displacement of the movable arm.

6. An instrument according to claim 3, wherein a fork is provided to define the minimum distance between said clamps, the fork being fixed to one of said clamps and having two arms between which the anvil is arranged.

7. An instrument according to claim 3, wherein, on that side of the anvil which is opposite the feed plate, there is provided an inclined plane to ensure the discharge of the sample blocks ejected from the clamps.

8. An instrument according to claim 1, wherein each of said sample blocks is a rectangular parallelepiped possessing a groove to receive a respective said sample end.

9. An instrument according to claim 1, wherein the loader comprises two parallel and identical slides having dimensions slidingly to receive the sample blocks, the distance between the adjacent edges of the two slides being substantially equal to the length of the sample to be tested.

10. An instrument according to claim 1, wherein the loader has a bottom part in which it comprises at least one stud, and at least one retaining plate operative to prevent the blocks stacked in the loader from falling and controlled by said stud, the instrument including two guides between which the loader is held perpendicular to the feed plate, the stud cooperating with a respective one of said guides to release the respective said retaining plate when the loader is positioned in said guides to permit the lowermost pair of sample blocks in said loader to fall onto the plate.

11. An instrument according to claim 1, including an inertia block which rests with its weight on the stack of blocks contained in the loader to descend towards the plate as the loader empties, and a fixed contact cooperable with the said inertia block to indicate when the loader is nearly empty.

12. An instrument according to claim 1, wherein the feed device comprises a jack and a fork which undergoes translational movement on the plate responsive to operation of the jack, said fork having two arms each cooperating with a respective one of a pair of sample blocks to be displaced.

13. An instrument according to claim 1, wherein at least one of the two clamps comprises a stop cooperable with the other clamp to define the minimum distance between the clamps.

14. An instrument according to claim 1, wherein the tensioning means comprises a reversible electric motor and a screw-and-nut system associated with said motor.

15. An instrument according to claim 14, wherein the motor drives the screw of the screw-and-nut system and the movable clamp is integral with the nut, there being provided a groove fixed relative to the frame and a stud slidable in said groove with said stud being carried by said nut.

16. An instrument according to claim 1, including a detector producing an electric signal to measure displacement of the movable clamp, the measurement being started when the tensile force becomes non-zero upon operation of the tensioning means.

17. An instrument according to claim 1, wherein the force detector comprises a dynamometric ring which is joined at one point to the frame and at least one stress gauge carried by the said ring to produce an electric measuring signal.

18. An instrument according to claim 17, including a rod which passes through the dynamometric ring and is integral with the fixed clamp, there being provided a rounded bearing surface inside the ring upon which the rod rests so as to be guided, with play, relative to the frame.

19. An instrument according to claim 18, which includes four stress gauges carried by the dynamometric ring and connected to form a bridge, the stress gauges being distributed in pairs at the ends of a diameter which is substantially perpendicular to the said rod passing through the ring.

* * * * *